(12) United States Patent
Eastwood

(10) Patent No.: US 6,524,110 B1
(45) Date of Patent: Feb. 25, 2003

(54) BODY WEIGHT SUPPORTS AND TEACHING AID

(76) Inventor: Owen Eastwood, 7 Bay View Court, St. Aubins Road, St. Helier, Jersey, JE2 4ZZ (GB)

( * ) Notice: Subject to any disclaimer, the term of this patent is extended or adjusted under 35 U.S.C. 154(b) by 16 days.

(21) Appl. No.: 09/609,081

(22) Filed: Jun. 30, 2000

(30) Foreign Application Priority Data

Jul. 3, 1999 (GB) .............................................. 9915534
Jul. 7, 1999 (GB) .............................................. 9915800

(51) Int. Cl.[7] .............................................. A63B 69/18
(52) U.S. Cl. ...................................................... 434/253
(58) Field of Search ................................ 434/247, 253; 280/842, 809, 812, 819, 11.36, 816; 128/80 C, 80 R, 80 Q, 80 F; 482/74, 75, 112

(56) References Cited

U.S. PATENT DOCUMENTS

| | | | | |
|---|---|---|---|---|
| 3,799,159 A | * | 3/1974 | Scott | 602/16 |
| 3,928,872 A | * | 12/1975 | Johnson | 2/22 |
| 4,408,600 A | * | 10/1983 | Davis | 128/80 R |
| 4,450,832 A | * | 5/1984 | Waddell | 2/22 |
| 4,522,199 A | * | 6/1985 | Waddell et al. | 602/23 |
| 4,759,570 A | | 7/1988 | Dandy, III | |

* cited by examiner

*Primary Examiner*—Derris H. Banks
*Assistant Examiner*—Kurt Fernstrom
(74) *Attorney, Agent, or Firm*—Trexler, Bushnell, Giangiorgi, Blackstone & Marr, Ltd.

(57) ABSTRACT

The invention relates to body supports and teaching aids particular for use during skiing. Skiing to greater or to lesser degrees imposes strains on the muscles of the skier causing fatigue and encouraging a skier to adopt an incorrect stance or posture not conducive to good and correct skiing. The object of the invention is to provide a simple and effective body support and teaching aid that is effective during skiing and does not need to be removed during a temporary cessation of activity but allows substantial freedom of movement of the legs during walking and sitting. This objective is met by a construction comprising a first (upper) member adapted for location against the thigh area of the leg, a second (lower) member adapted for location against the calf area of the leg, a pivotal connection between the first and second members, the second member being connectable to the boot of a user, load bearing means located on the support to provide a resistance to pivotal movement between the first and second members, and said load bearing means being deactivatable to permit substantially free pivotal movement between the first and second members.

21 Claims, 5 Drawing Sheets

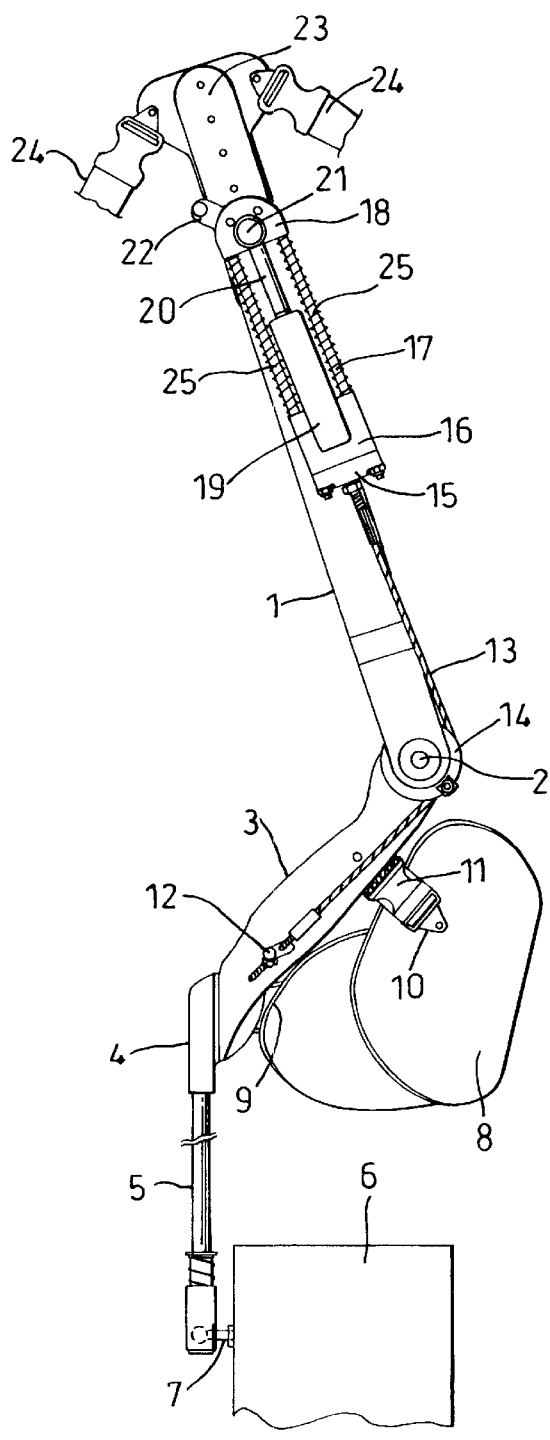
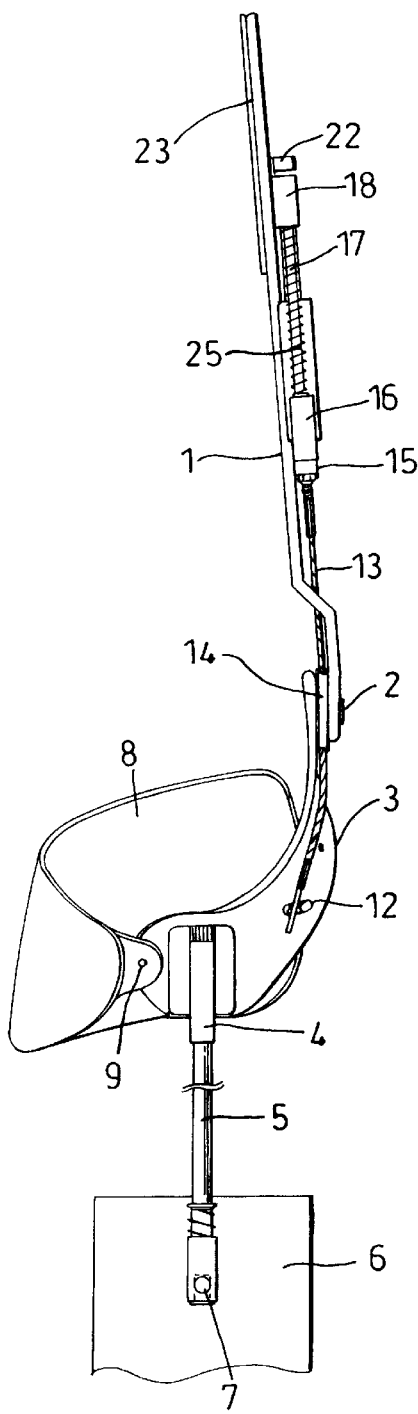
Fig. 1
Fig. 2

BODY WEIGHT SUPPORTS AND TEACHING AID

This invention relates to body supports and teaching aids, particularly, but not necessarily exclusively for use during skiing.

Skiing is a sport enjoyed by considerable numbers of skiers over a wide age group. Even relatively gentle skiing down ski runs that are not severe and better suited to less experienced skiers imposes considerable strains on the muscles of the skier, particularly in the legs, resulting from the skier adopting an incorrect stance or posture along with the repeated impacts of the skis with uneven compacted snow or ice causing a bouncing effect that the skier must combat by repeatedly bending the legs, whilst at the same time the legs must continue to support the skier. The more severe is a ski slope, the greater is the stress on the legs, and consequently all skiers, whether young and with leg muscles not yet fully developed, in their prime and wanting to ski for prolonged periods in difficult conditions, or more elderly and with leg muscles past their prime, can benefit from the use of body weight supports that assist in setting the skier in a correct position.

Body weight supports and teaching aids must not only allow a part of the body weight of the skier to be removed from the skier's legs, but also must allow the legs to bend at the knee, and additionally must not inhibit a skier from moving the hips laterally to incline the legs to set the skis on edge and allow the skier to implement turning movements to the left and to the right.

There have been earlier proposals for providing leg supports, where skiers employ poles connected to the skiers boots and linked by springs at the upper ends of the poles to a harness worn by the skier. Not only is such a construction cumbersome, springs of conventional construction have a variable load resistance as they are stretched or compressed, and consequently give a variable supporting force that is not conducive to good skiing. Additional to this, prior art constructions do not give any effective assistance in putting a skier into a correct skiing posture. Such a construction has the further disadvantage in stopping the skier from bending and flexing the legs when not skiing and consequently a skier cannot board such as ski lifts or chairs with the support mean fitted for use. Consequently the construction must be dismantled to allow a skier to sit and walk normally, and reassembled at the top of a ski slope. The construction involved is inevitably visible, and aesthetically unattractive. Whilst giving support to the skier, such constructions offer nothing by way of assistance in setting the skier in a correct position or posture.

The object of the invention is to provide a body weight support and teaching aid, particularly for use in skiing, that is effective and avoids those disadvantages mentioned above and provides still further advantages.

According to the present invention a body weight support comprises a first (upper) member adapted for location against the thigh area of the leg, a second (lower) member adapted for location against the calf area of the leg, a pivotal connection between the first and second members, the second member being connectable to the boot of a user, load bearing means located on the support to provide a resistance to pivotal movement between the first and second members, and said load bearing means being deactivatable to permit substantially free pivotal movement between the first and second members.

Preferably, the connection between the second member and the boot is a rod fitted to a socket at the lower end of the second member and the socket and the rod may be correspondingly threaded, the rod extending to a snap fit connection on the boot, preferably at the rear of the boot.

With the majority of able bodied skiers, it is desirable to provide two supports, one for each leg, with the upper ends of the supports connected by a strap or other member extending around and below the posterior of the skier.

With a disabled skier, such as those with one leg only, two support members can be provided to locate to either side of the one leg, and a strap or other member extending around the back of the thigh and connecting the upper ends of the two supports.

The upper member may be formed as a generally straight elongate, eg rectangular bar, to locate on the outside of the respective leg of the user, and is provided with a bracket at its upper end for straps to engage around the upper leg or thigh area, in addition to a strap to pass around the posterior of the user. The lower member extends from the pivot with an upper member to a curved and plate-like lower part to locate behind the calf muscle of the respective leg of the user, and a lower fixing strap may be attached to the lower end of the lower support. Desirably, quick release fittings are provided on all of the straps. A quick release fitting may be located on a shin support or protector, attached to the lower member and adapted to overlie the shin of the user.

In one possible form of construction, a load bearing means is attached to the outer surface of the upper support. Preferably, the load bearing means is such that when active it provides a substantially constant force, such as can be provided by a gas strut. Thus, the gas strut may be located in a housing on the upper leg support, there being a cable connecting the gas strut to the lower leg support, said cable passing around a guide at the pivotal connection between the upper and lower members. The cylinder of the gas strut may be attached to a cradle secured to the upper member, below which is a cable attachment member. The cable attachment member has two guide rods extending through corresponding holes in the cradle which extend to a bridging member connected to and extending across the tops of the guide rods. Desirably, in the bridging member is a rotatable stop, able to be rotated from a position where it forms an abutment to engage the top of a piston rod extending from the cylinder, to a position where a through hole in the stop is aligned with the piston rod, to allow the passage of the piston rod therethrough. With the rotatable stop in a position where its hole is aligned with the piston rod of the gas strut, the bridging member could slide down the guide rods, and with the piston rod engaging the hole, the rotatable member could not be rotated to activate the support means. Therefore, between the cradle and the bridging member, the guide rods may have surrounding coil return springs to hold the bridging member in an elevated position with the rotatable member clear of the top of the piston rod. An alternate possibility is to have a coil spring surrounding the or each gas strut, and bearing against the cradle and the bridging member.

When the support means is activated, the user is immediately faced with the full force of the or each gas strut as he or she first settles into a skiing position. It is therefore preferred to have the or each gas strut slidably mounted in the cradle, and for a coil spring to be provided below the or each gas strut. As a result, there is a cushion effect provided by the compressing of the coil spring below the gas strut, and when the spring is compressed, the gas struts then come into play.

Whilst the presence of coil springs can provide a useful supplement to the load bearing characteristics of the or each gas strut, they should be of a rating such that with the load bearing means deactivated, they do not provide a major resistance to the freedom of the upper and lower members to pivot, and hence allow the skier to walk and sit relatively normally without the need to remove the body support means.

Simple and unobtrusive lever means may be provided to rotate the stop means.

Thus, with two body weight support means attached to the outside of each leg and interconnected by the strap at their upper ends, with, if the skier requires it, suitable padding between the legs and the supports, the skiers overtrousers can be put on, totalling hiding the support from view, and yet easily activated by the movement of the lever on the rotatable stop through the overtrousers. The means of the invention can be fitted in the privacy of the skiers room, leaving the skier with nothing more to do when putting on ski boots but to snap fit the bottom of the rod to the fitting on the boot.

When fitted but not activated, the skier has substantially full leg mobility, allowing normal walking and sitting, and when required to be activated such as at the top of a ski slope, simple movement of the lever puts the body support means in an active state. Thus, as the legs of the skier bend at the knees, and the body of the skier descends, pivoting of the upper and lower members causes a downward force on the cable that is resisted by the gas strut as the bridging member is drawn downwards attempting to push the piston into the cylinder, as a consequence of which, a proportion of the body weight of the skier is transferred through the posterior strap, the support mechanism and the rod attached to the lower member to the boot of the skier.

To provide a skier with a means of increasing or decreasing the degree of support provided, two or more gas struts may be provided, one, both or all of which can be selectively rendered active, to give a skier the ability to employ one, or more gas struts.

In addition to selective activation and deactivation, it is a most important facet of the invention, that when a skier is not actually skiing, but intends to ski, removal of the support means is avoided.

It will readily be understood that the support exemplified above can be reversed in the sense of placing the load bearing means on the lower support member and running the cable around the cable guide to a fixing point on the upper support member.

In both circumstances, the fixing point for the cable is preferably provided with an adjuster to take any slack out of the cable and ensure that the load bearing means is activated when the skier effects a downward or sitting action. In addition to giving body weight support the instant a skier assumes the position for skiing, correct setting of the cable, governing when a further downward movement of the body is attempted, has the considerable advantage of causing the skier to assume a technically correct posture for skiing. More than this and during skiing itself, the constant force resisting body downward movement acts as a most effective cushion or shock absorber to help the prevention of wear and damage particularly to the knees of the skier.

With the load bearing means deactivated, the skier can walk and sit with relative ease, and when ready to ski, by a simple rotation of the stop means, can easily and fully activate the load bearing means, to give considerable support to the body weight of the skier by its transfer to the skier's boot, and hence eliminate a substantial proportion of the strain otherwise imposed on the muscles of the skier's legs, whilst at the same time maintaining substantial leg and knee mobility, necessary to enable a skier to ski correctly.

Several embodiments of the invention will now be described with reference to the accompanying drawings in which:

FIG. 1 is a side elevation of a first embodiment of body weight support and teaching aid in accordance with the invention;

FIG. 2 is a rear elevation of the support of FIG. 1;

Figure 3:
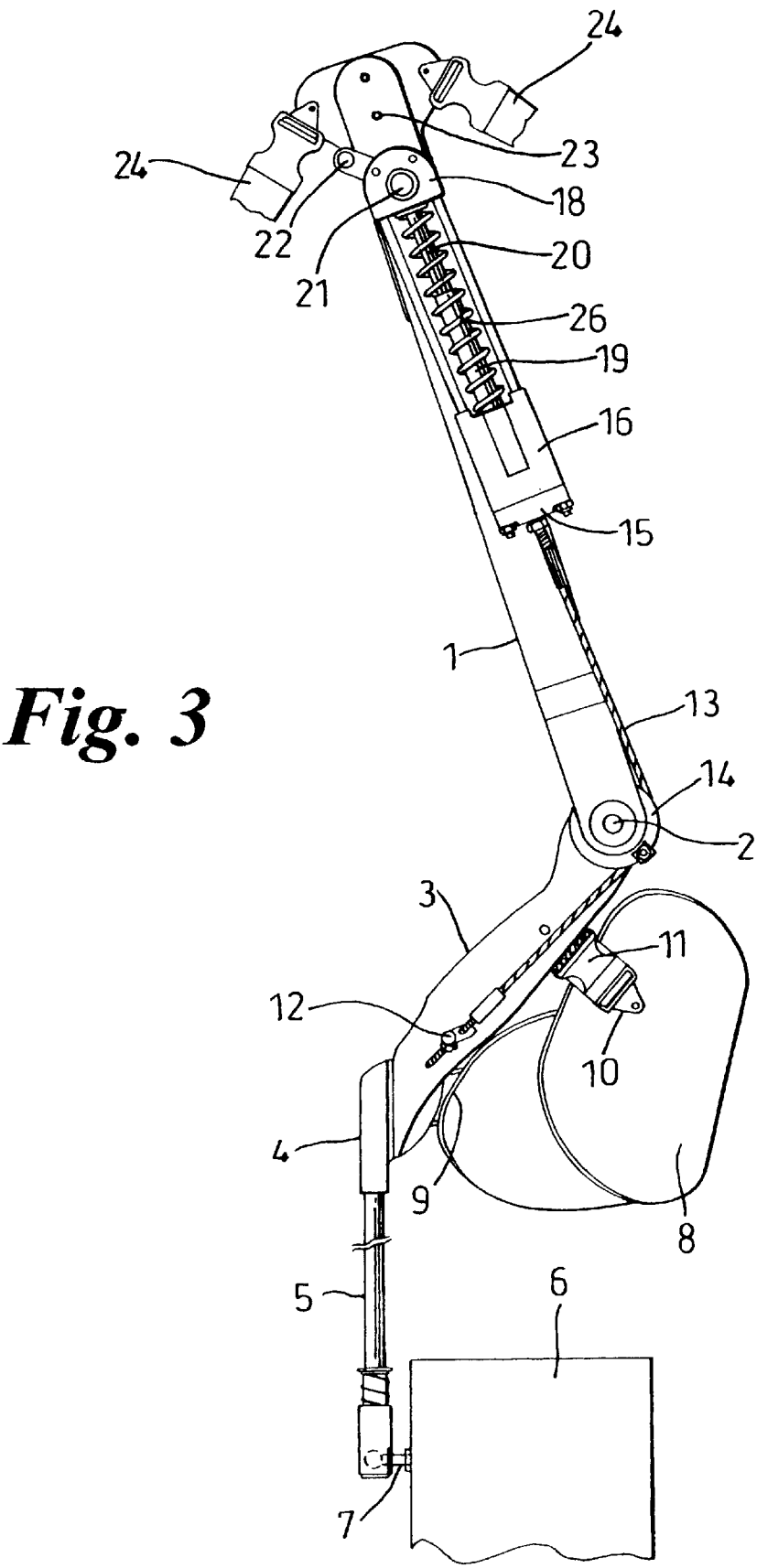
Figure 4:
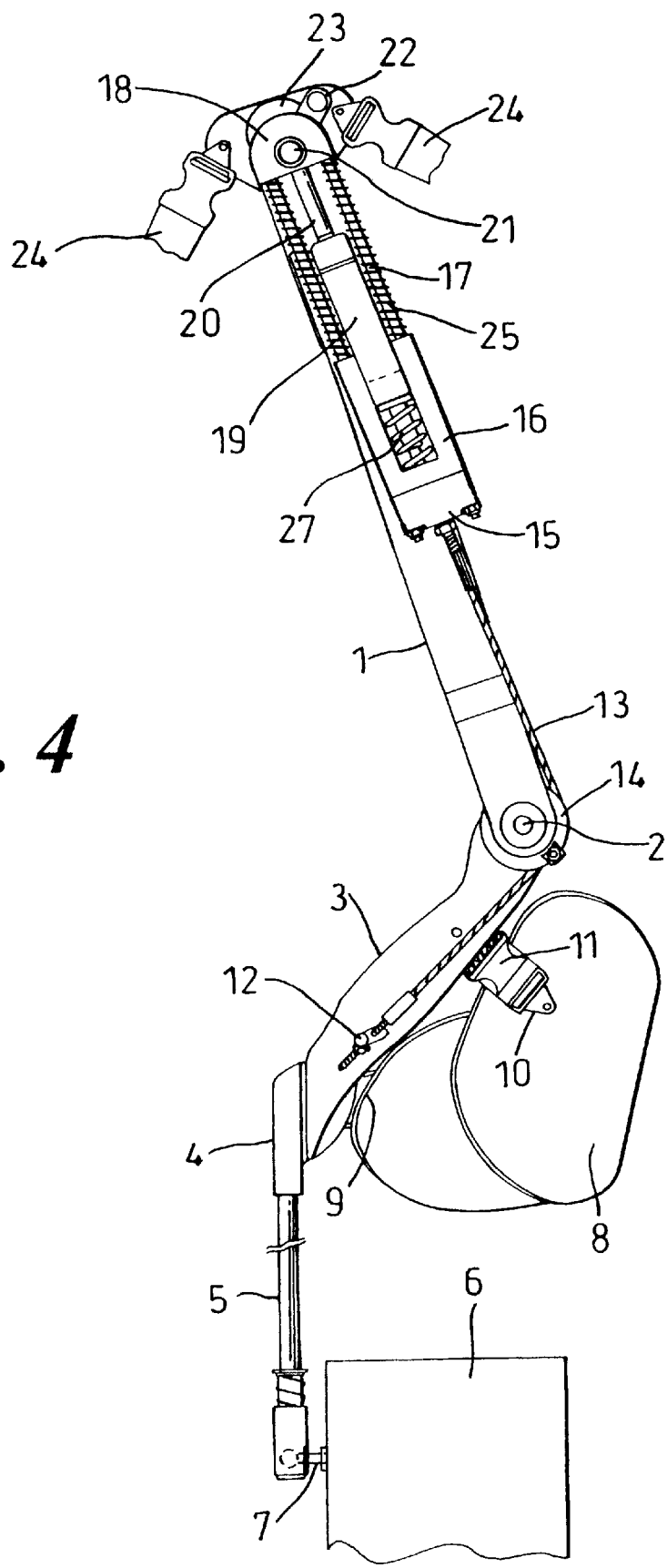
Figure 5:
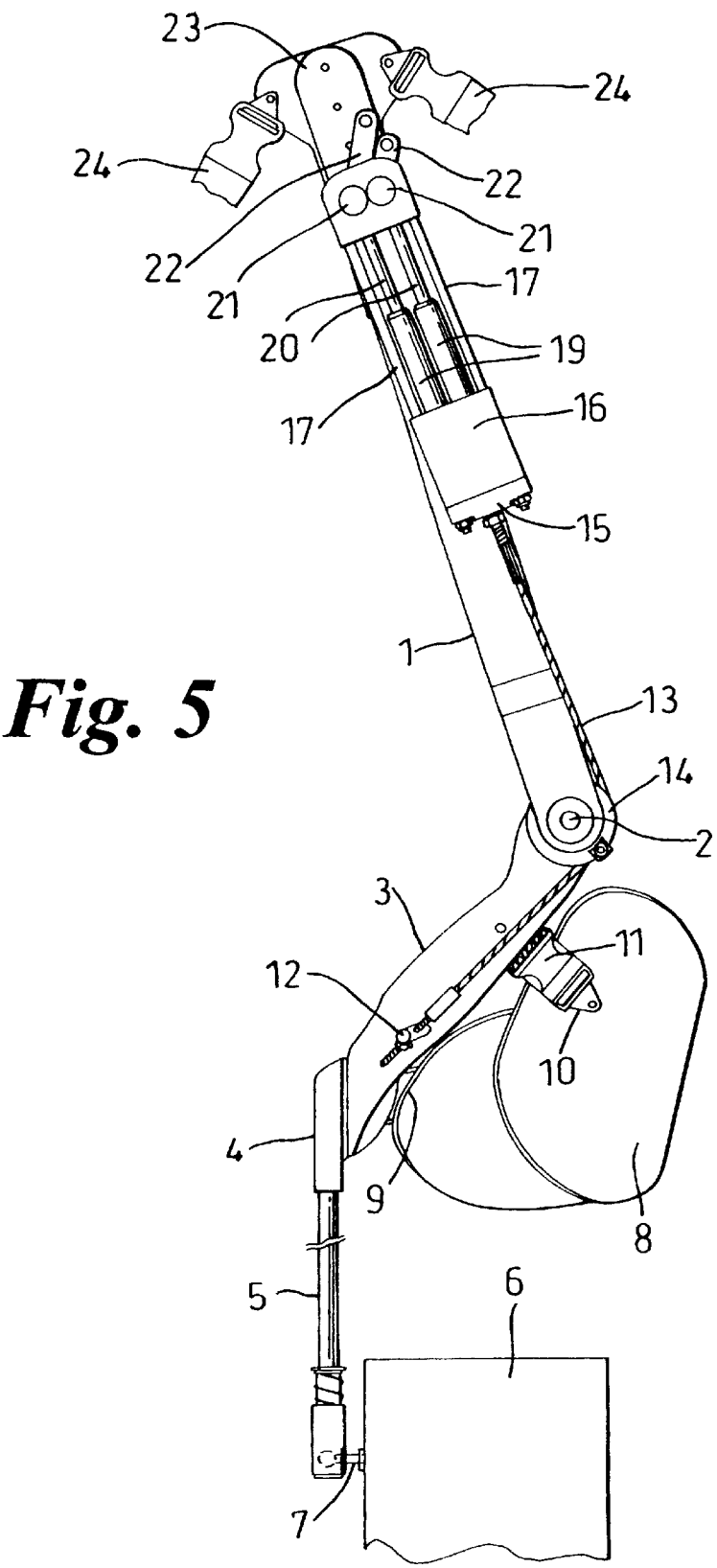
Figure 6:
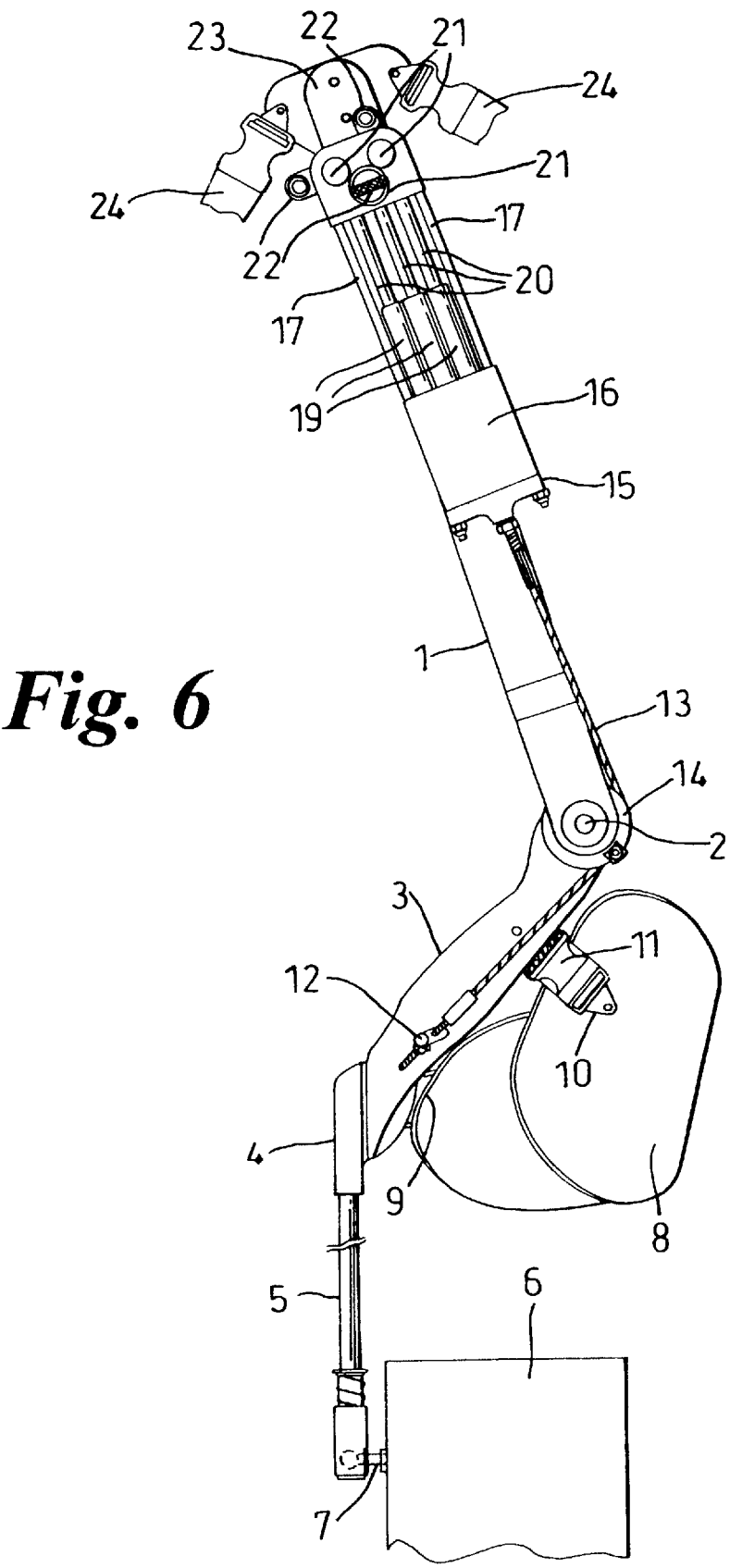

FIG. 3 corresponds to FIG. 1 but shows a second embodiment of body weight support and teaching aid in accordance with the invention;

FIG. 4 corresponds to FIG. 1 but shows a third embodiment of body weight support and teaching aid in accordance with the invention;

FIG. 5 corresponds to FIG. 1 but shows a fourth embodiment of body weight support and teaching aid in accordance with the invention; and FIG. 6 corresponds to FIG. 1 but shows a fifth embodiment of body weight support and teaching aid in accordance with the invention.

It will be understood that in the following description of the illustrated embodiments of the invention, like parts are given the same reference numbers.

In FIGS. 1 and 2 a body weight support or teaching aid has a first (upper) member 1 for location against the thigh of the user, in the form of a rectangular bar-like member of a low weight, high strength material, of an appropriate metal or plastics material. At its lower end, the upper member 1 has a pivotal connection 2 to a second (lower) member 3 for location behind the calf of the user. Towards its lower end, the lower member 3 has a socket 4 to receive a rod 5 able to be connected to a ski boot 6 by a detachable or snap-fit connector 7.

On the lower member is a shin support or protector 8 attached at one end 9 directly to the lower member, and having a quick release fitting 10 at its free end for attachment to a co-operating fitting 11 on the lower member, to hold the lower member in position against the calf of the user.

Attached to the outer face of the lower member by an adjustable connector 12, is a cable 13 that extends around a pulley 14 at the pivot 2 between the upper and lower members 1,3 to a cable attachment member 15 below the lower end of a cradle 16 secured to the upper end of the upper member 1. Guide rods 17 located on the cable attachment 15 extend through holes in the cradle 16 and extend to and engage the bridging member 18.

Also located on the cradle is a gas strut 19, the piston rod 20 of which extends to the bridging member 18, on which is located a rotatable stop means in the form of a cylindrical plug 21 having an operating lever 22, the plug having a through hole to co-operate with the end of the piston rod.

Extending from the bridging member is a support bar 23 for quick fit connectors 24 for belts to pass around the thigh of the user to hold the upper members in place, and for a belt to pass around the posterior of the user.

Thus, with a support as above described attached to the leg of a user, and with the plug rotated to bring its through hole into register with the piston rod, the support means is inactive and bending of the legs of the user during walking or sitting results in the piston extending into and through the hole, with no resistance. This allows the user to walk and to sit relatively normally, without the need to remove the support means.

When skiing is about to commence, simple rotation of the plug 21 by its lever 22 takes the hole out of register with the piston rod. Thus, as the legs of the skier bend at the knees, and the body of the skier descends, pivoting of the upper and lower members causes a downward force on the cable 3 that is resisted by the gas strut 19 as the bridging member 18 is drawn downwards attempting to push the piston into the cylinder, as a consequence of which, a proportion of the body weight of the skier is transferred through a posterior strap, the support mechanism and the rod 5 attached to the lower member to the boot 6 of the skier.

A wide selection of gas struts of different ratings is available, from which a selection can be made to suit particular weights of user and to suit different degrees of support preferred by a user.

To ensure that the plug 21 can be rotated, and as is shown in FIG. 1, coil compression springs 25 may be provided on each guide rod to hold the bridging member in an elevated position when the user is upright, to hold the plug 21 clear of the piston rod 20. Care must however be exercised in the selection of the spring ratings to ensure that when deactivated, the springs of themselves do not offer much by way of resistance to the pivoting of the upper and lower members of the support. As is illustrated in FIG. 3 a single compression spring 26 may be employed surrounding the gas strut 19 for essentially the same purpose.

As is illustrated in FIG. 4, the gas strut 19 may be slidably mounted on the cradle 16, and a compression spring 27 located below the gas strut 19 and lying between it and the cradle. Thus, on activating the support means, the coil spring 27 allows a first downward movement of the gas strut as the skier settles into a skiing position, thereby providing a cushion effect, and once compressed, the gas strut then comes into play to assist in the supporting of the weight of the skier. Here, the snap fit connector 10, 11 may be replaced by a hook and loop connector.

As a means of providing a user with an ability to adjust the degree of support provided by the support means, there may be provided two gas struts 19 as shown in FIG. 5, or three gas struts 19 as is shown in FIG. 6. Here, the bridging member may have a number of rotatable plugs, each with a co-operating hole for a respective piston rod, and each with an operating lever 22.

In FIG. 5, the two struts may have the same rating or may have different ratings, and similarly with the three struts of FIG. 6. Thus, by activating one, the other or both of the gas struts of FIG. 5, variable degrees of support can be selected at will, and with FIG. 6, still further variations are provided by enabling each gas strut to be activated individually, or pairs of gas struts, or all of the gas struts simultaneously.

When considering FIGS. 5 and 6, it will be fully understood that additional support may be provided by employing compression springs after the manner of the teachings of FIGS. 1 to 4.

What is claimed is:

1. A body weight support configured for connection to a boot of a user, said body weight support characterized by a first upper member adapted for location against the thigh area of the leg, a second lower member adapted for location against the calf area of the leg, a pivotal connection between the first and second members, the second member being connectable to the boot of the user to form a connection between the second member and the boot, load bearing means located on the support to provide a resistance to pivotal movement between the first and second members, and deactivating means configured to provide that said load bearing means is deactivatable to permit substantially free pivotal movement between the first and second members, wherein said deactivating means is actuateable to provide that the load bearing means is inactive through a full range of motion and remains inactive while the user walks and sits.

2. A body weight support as in claim 1, characterized in that the connection between the second member and the boot is a rod fitted to a socket at the lower end of the second member and the socket and the rod are correspondingly threaded, the rod extending to a snap fit connection on the boot.

3. A body weight support as in claim 1, characterized in that strap means are provided to hold the support means to the leg of the user.

4. A body weight support as in claim 3, characterized in that strap means are provided to extend around the posterior of the user.

5. A body weight support as in claim 1, characterized in that the upper member is formed as a generally straight elongate, rectangular bar, to locate on the outside of the respective leg of the user, and is provided with a bracket at its upper end for straps to engage around the upper leg or thigh area, in addition to a strap to pass around the posterior of the user.

6. A body weight support as in claim 1, characterized in that the lower member extends from the pivot with an upper member to a curved and plate-like lower part to locate behind the calf muscle of the respective leg of the user, and a lower fixing strap is attached to the lower end of the lower support.

7. A body weight support as in claim 3, characterized in that quick release fittings are provided on all of the straps.

8. A body weight support as in claim 3, characterized in that the strap means to hold the lower part to the leg of the user serves as a shin support or protector.

9. A body weight support as in claim 1, characterized in that the load bearing means is at least one gas strut.

10. A body weight support as in claim 9, characterized in that the gas strut is located in a housing on the upper leg support, there being a cable connecting the gas strut to the lower leg support, said cable passing around a guide at the pivotal connection between the upper and lower members.

11. A body weight support as in claim 9, characterized in that the gas strut includes a cylinder and the cylinder of the gas strut is attached to a cradle secured to the upper member, below which is a cable attachment member.

12. A body weight support as in claim 11, characterized in that the cable attachment member has two guide rods extending through corresponding holes in the cradle which extend to a bridging member connected to and extending across the tops of the guide rods.

13. A body weight support as in claim 12, characterized in that in the bridging member is a rotatable stop, able to be rotated from a position where it forms an abutment to engage the top of a piston rod extending from the cylinder, to a position where a through hole in the stop is aligned with the piston rod, to allow the passage of the piston rod therethrough.

14. A body weight support as in claim 12, characterized in that between the cradle and the bridging member, the guide rods have coil return springs to hold the bridging member in an elevated position when the skier is upright.

15. A body weight support as in claim 12, characterized in that a coil spring is provided surrounding the gas strut and extending between the cradle and the bridging member.

16. A body weight support as in claim 12, characterized in that the gas strut is slidably mounted in the cradle and a coil spring is provided below the cylinder and bearing on the cradle.

17. A body weight support as in claim 13, characterized in that lever means are provided to rotate the stop means.

18. A body weight support as in claim 9, characterized in that said body weight support comprises a plurality of similar gas struts.

19. A body weight support as in claim 9, characterized in that said body weight support comprises a plurality of different gas struts.

20. A body weight support as in claim 10, characterized in that the cable is attached to the lower support member with provision for adjustment.

21. A system of two body weight supports, each configured for connection to a boot of a user, each of said body weight supports characterized by a first upper member adapted for location against the thigh area of the leg, a second lower member adapted for location against the calf area of the leg, a pivotal connection between the first and second members, the second member being connectable to the boot of the user to form a connection between the second member and the boot, load bearing means located on the support to provide a resistance to pivotal movement between the first and second members, and deactivating means configured to provide that said load bearing means is deactivatable to permit substantially free pivotal movement between the first and second members, wherein said deactivating means is actuateable to provide that the load bearing means is inactive through a full range of motion and remains inactive while the user walks and sits.

* * * * *